US005466460A

United States Patent [19]

McMahon et al.

[11] Patent Number: 5,466,460
[45] Date of Patent: Nov. 14, 1995

[54] CONTROLLED RELEASE MICROCAPSULES

[75] Inventors: William A. McMahon; Chel W. Lew, both of San Antonio, Tex.; Keith L. Branly, Brandon, Fla.

[73] Assignee: Micro Flo Company, Mulberry, Fla.

[21] Appl. No.: 160,276

[22] Filed: Dec. 2, 1993

Related U.S. Application Data

[62] Division of Ser. No. 858,130, Mar. 27, 1992, Pat. No. 5,292,533.

[51] Int. Cl.$^6$ .................................................. A01N 25/28
[52] U.S. Cl. ................ 424/408; 71/DIG. 1; 424/418; 424/499; 424/500
[58] Field of Search ................................ 424/408, 418, 424/499, 500; 428/402.2; 264/4.1, 4.3; 71/DIG. 1

[56] References Cited

U.S. PATENT DOCUMENTS

| | | | |
|---|---|---|---|
| 3,460,972 | 8/1969 | Nack | 427/214 |
| 3,520,821 | 7/1970 | Striley et al. | 428/402.2 |
| 3,872,024 | 3/1975 | Horger | 424/450 X |
| 3,886,084 | 5/1975 | Vassiliades | 428/402.22 |
| 3,943,063 | 3/1976 | Morishita et al. | 424/418 |
| 3,956,172 | 5/1976 | Saeki et al. | 264/4.3 |
| 4,082,688 | 4/1978 | Egawa et al. | 264/4.3 |
| 4,251,195 | 2/1981 | Suzuki et al. | 425/6 |
| 4,269,729 | 5/1981 | Maruyama et al. | 428/402.22 |
| 4,273,672 | 6/1981 | Vassiliades | 264/4.1 |
| 4,303,548 | 12/1981 | Shimazaki et al. | 264/4.7 |
| 4,376,113 | 3/1983 | Suglia et al. | 424/494 |
| 4,394,287 | 7/1983 | Scarpelli | 424/494 X |
| 4,402,856 | 9/1983 | Schnoring et al. | 428/402.22 |
| 4,460,563 | 7/1984 | Calanchi | 424/494 |
| 4,460,722 | 7/1984 | Igarashi et al. | 523/206 |
| 4,481,157 | 11/1984 | Morishita et al. | 264/4.1 |
| 4,696,822 | 9/1987 | Matsamura et al. | 424/490 |
| 4,808,408 | 2/1989 | Baker et al. | 424/408 |
| 4,808,408 | 2/1989 | Baker et al. | 424/408 |
| 4,851,227 | 7/1989 | Markus et al. | 424/419 |
| 4,946,624 | 8/1990 | Michael | 252/315.2 |
| 4,961,871 | 10/1990 | Michael | 252/174.11 |
| 5,112,688 | 5/1992 | Michael | 428/402.2 |
| 5,292,533 | 3/1994 | Lew et al. | 424/408 |

FOREIGN PATENT DOCUMENTS 51-112526  10/1976  Japan .

OTHER PUBLICATIONS

Usher et al., *Entomologia Experimentalis et Applicata*, 52(2) 1989, pp. 119–134 (abstract).
"EPA Calls for Voluntary Risk Reduction for Granulars", *Pesticide & Toxic Chemical News*, pp. 22–23 (May 27, 1992).

*Primary Examiner*—John C. Bleutoe
*Assistant Examiner*—Robert H. Harrison
*Attorney, Agent, or Firm*—Banner & Allegretti, Ltd.

[57] ABSTRACT

Microcapsules are prepared by encapsulating a core material with a capsule shell wall containing glutaraldehyde crosslinked gelatin and at least one water soluble plasticizer that reduces the permeability of the crosslinked gelatin. Optionally, the capsule shell wall also contains a feeding deterrent that dissuades accidental ingestion of the microcapsule. Upon exposing the microcapsules to water, the plasticizer is removed making the shell wall permeable whereby the encapsulated core material is released. Materials such as insecticides, herbicides, plant growth regulating agents, and fungicides may be encapsulated and released at a controlled location, time and rate.

13 Claims, No Drawings

5,466,460

CONTROLLED RELEASE MICROCAPSULES

This is a divisional of application Ser. No. 07/858,130 filed on Mar. 27, 1992, now U.S. Pat. No. 5,292,533.

BACKGROUND OF THE INVENTION

1. Field of the Invention

The present invention relates to a microencapsulation shell system which provides for the controlled release of the material encapsulated thereby. Microcapsules, methods of manufacture, and methods of using the microcapsules are particularly contemplated by the invention.

2. Description of Related Art

Timing is everything in many technologies. That is particularly true for chemically-based technologies such as agriculture, insecticides, and fungicides where contact or inadvertent ingestion may pose serious health risks to humans and animals. Paraquat is one example of a useful chemical that poses a serious health risk due to inadvertent ingestion, inhalation, or contact. Such chemicals should be enclosed and protected from at least the point of manufacture, through transport, and until the chemical is loaded into some form of wet or dry product applicator. Because such contact has been generally unavoidable for most chemical products, a complex scheme of regulation has been established to control the handling and exposure risks to humans as well as nontarget animals. The art has faced a long standing need for a means of preventing contact between useful but potentially hazardous chemicals and nontarget organisms without reducing the efficacy of the chemical agent.

Another situation where timing is important is where chemically active agents must maintain an extended presence to be effective or must migrate from an applied position to a more desired location. An example of such a chemical is the soil insecticide diazinon which is a contact pesticide that used to be available for application to sod farms and golf courses in the form of solid granules on a corn cob grit carrier. Contact with water would dissolve the granule from the carrier and wash the pesticide into the soil. Diazinon was quite effective at controlling soil-borne pests that would otherwise damage the grass.

Unfortunately, the diazinon-containing granules were applied during the day and exhibited a particle size that was large enough to sit on top of the turf thatch. Birds flying overhead in search of food could still see the granules and would mistakenly them as food. The Environmental Protection Agency recently prohibited further use of diazinon for sod farms and golf courses due to the unacceptably high level of avian mortality from these uses. It would be desirable to have a means for applying granulated contact insecticides during normal daylight hours with protection against avian feeding but yet be able to release the insecticide when avian feeding does not pose a risk of mortality due to accidental consumption.

One possible approach suggested by Michael U.S. Pat. No. 4,946,624 for laundry products is a crosslinked glutaraldehyde microcapsule having a core material, preferably perfume, surrounded by a capsule shell wall of coacervated gelatin and gum arabic that have been crosslinked with glutaraldehyde. This shell wall can have small "particles" of 0.1–25% of the core diameter that can be "activated" with heat from the drier or warm water from the wash or rinse cycle in a clothes washing machine to form discrete holes in the shell. The particles can be liquids that will volatilize from heat or solids that will dissolve in wash or rinse water to form pores or holes through which the hydrophobic core material escapes. No specific list of solid inclusion particles is provided. Perfumes, flavors, pharmaceutical materials and agricultural chemicals in general are taught to be useful for the encapsulation.

In many applications, however, the core material must be and is desirably hydrophobic. The wall of the microcapsule must be able to form porosity in ambient or cold water and do so without affecting the viscosity of the solution or leave residues that could clog spray nozzles or tubing.

In other applications, microcapsule walls made of gelatin and gum arabic crosslinked with glutaraldehyde are not sufficiently impermeable to restrain the core material and remain compatible with a water carrier. This is particularly true for some hydrophobic materials including herbicides and plant growth regulating agents, insecticides, and fungicities that have a particularly strong solvation ability. Some form of better encapsulation system is needed to form such materials into microcapsules that will be impermeable to the core material.

It would be desirable to have a microencapsulated system that could be used for herbicides and plant growth regulating agents, insecticides, and fungicides without modification of the handling, mixing, or application methods currently in use.

It would also be useful to have a microencapsulation system that would encapsulate hydrophilic materials as well as a broad spectrum of hydrophobic materials including those of high salvation ability yet permit release of the encapsulated material upon contact with water having a temperature of less than about 100° F. (38° C.).

SUMMARY OF THE INVENTION

It is an objective of the invention to provide microencapsulated agents that provide an increased level of safety against contact hazards during packaging and transport with release of the encapsulated material upon exposure to water having a temperature of less than about 100° F. (38° C.).

It is an objective of the invention to provide a microencapsulation system that can be used for a variety of agricultural chemicals without significant modification of the existing application methods.

It is an objective of the invention to provide a microencapsulation system for hydrophilic core materials in a dry form or suspended in a hydrophobic carrier liquid as well as hydrophobic core materials that will be completely impermeable or at least exhibit a sufficiently low level of permeability to the encapsulated materials that they can be made, stored, and used without significant risk of accidental contact with the core material.

In accordance with these and other objectives that will become apparent from the description herein, the invention is directed to the manufacture, use, and composition of controlled release microcapsules comprising a core material coated by an impermeable shell made of a glutaraldehyde cross-linked gelatin containing a water-soluble plasticizer selected from starches, sugars, corn syrup solids, cyclodextrins, maltodextrins, glycerin, sorbitol, water soluble polymers such as polyvinyl alcohol and polyethylene oxide which inhibits permeation of hydrophobic materials through the shell wall. Upon exposure to water, the plasticizer dissolves from the shed wall and forms a microporous shell wall that does not exhibit gaps or openings through the shed but which is uniformly porous for the escape of core material. Various levels of plasticizer will permit the microcapsule to be tailored for applications requiring immediate release of the entire core material as well as for applications requiring a gradual release of the core material over an extended time period. Birds and small ground animals can be dissuaded from feeding on the microcapsules by incorporating a cucurbitacin-containing feeding deterrent into the shell or coating the wet microcapsules with such feeding deterrents. Alternatively, the microcapsules can be made sufficiently small that they are not readily visible from overhead by flying birds and will not, therefore, be mistaken for food.

By the present invention, the contact hazards of a wide variety of agricultural chemicals including herbicides and other plant regulating agents, insecticides, and fungicities can be reduced while affording greater control over the timing and nature of the release of the encapsulated material. The microcapsule form carries the active chemical ingredients in a particle form that eliminates the problems traditionally associated with inhalation of vapors, aerosols, or fine dusts. The microcapsule shell prevents release of the hazardous core material until the microcapsule is soaked in water such as occurs in a spray tank or from dew as occurs in evenings when the risks of contact or ingestion are substantially reduce.

DETAILED DESCRIPTION

The microcapsules of the invention comprise a core material covered by a capsule shell. Core materials intended for encapsulation include hydrophilic materials in a dry form or suspended in a hydrophobic solvent as well as hydrophobic insecticides, herbicides and plant growth regulating agents, fungicides, insect attractants such as insect sex and alarm phermones, insect repellents such as N,N-diethyl-m-toluamide or deet; or combinations of any of these. Hydrophilic chemicals for the core are encapsulated as dry crystals, dry powders consisting essentially of the active chemical agent or comprising the chemical agent in combination with a solid carrier component such as a polysaccharide gum like carrageenan gum, xanthan gum, or guar gum.

Examples of insecticides that can be used as core materials for the present invention include solid and liquid forms of the carbamates (e.g., carbaryl, aldicarb, methomyl, carbofuran, bendiocarb, oxamyl, thiodicarb, trimethylcarb, and O-sec-butylphenylmethyl carbamate); organophosphates (e.g., phorate, terbufos, fonophos, isofenphos, ethoprop, fenamiphos, disulfoton, malathion, parathion, demeton, dimethoate, chlorpyrifos, diazinon, phosmet, and O,O-dimethyl-O-4-nitro-m-tolyl thiophosphate); rotenone; neem oil or azadoractin; natural or synthetic pyrethrins; the halogenated hydrocarbons (e.g., endrin, aldrin and its epoxide, dieldrin, heptachlor, DDT, BHC, lindane, chlordane, methoxychlor, DDD, TDE, and the polychlorinated biphenyls); *Bacillus thuringiensis*; and insecticidal viruses (e.g., entomopathic viruses such as *bacculo*). Microcapsules containing insecticides should have a particle size within the range from about 50 µm to about 5,000 µm, preferably within the range from about 300 µm to about 1,000 µm.

Examples of herbicides and plant growth regulating agents for the invention include paraquat, glyphosate, diphenyl ether-series herbicides such as P-nitrophenyl-2,4,6-trichlorophenyl ether, carbamate series herbicides containing S-P-chlorobenzyldiethyl carbamate and chlorinic-acid series herbicides. Microcapsules containing herbicides should have a particle size within the range from about 50 µm to about 5,000 µm, preferably within the range from about 300 µm to about 1,000 µm.

Examples of fungicides that will benefit from the present invention include organic sulfur fungicides such as zinc ethylene bis(dithiocarbamate); organic chlorine fungicides such as 4,5,6,7-tetra-chlorophthalide (chlorothalonil); and organic phosphorus fungicidessuch as O-ethyl-S,S-diphenyl dithiophosphate. For application to the grass of golf courses and sod farms, atrazine, trifluralin, phenoxy compounds (2,4-D salts and amines, MCPA, etc.) are particularly useful for the present invention. Microcapsules containing fungicides should have a particle size within the range from about 50 µm to about 5,000 µm, preferably within the range from about 300 µm to about 1,000 µm.

The capsule wall comprises: (a) a glutaraldehyde-crosslinked gelatin plasticized witha water soluble plasticizer which reduces the permeability of the crosslinked gelatin; and (b) an optional feeding deterrent containing a cucurbitacin. The gelatin and crosslinking glutaraldehyde components have been thoroughly described in, inter alia, U.S. Pat. Nos. 4,273,672; 4,808,408; and 4,946,624 the disclosures of which are herein incorporated by reference.

In general, plasticizers can be used to reduce the brittleness of a capsule wall or inhibit transfer of the core material through the shell wall by rendering the capsule wall less permeable to gases and/or liquids. In the present invention, the plasticizers aid in reducing the permeability of the gelatin shell after crosslinking to and reduce the permeation rate of volatile organic liquids, e.g., trichloroethylene, used as solvents for hydrophobic organic liquid core materials.

A plasticizer is also a material which forms a homogeneous mixture or solution in which molecules of the plasticizer and molecules of the gelatin are intimately and thoroughly admixed such that the plasticizer changes the properties of the crosslinked gelatin. The plasticizer and gelatin do not retain identity as discrete particles and do not form the type of pores found in Michael U.S. Pat. No. 4,946,624. The porosity of the present invention does not exhibit macroscopic holes or openings, but is finer and more uniform resulting in a microcapsule that is well suited to core materials that benefit from extended periods during which the core material is released.

Upon exposure to water, plasticizer molecules dissolve from the capsule wall and form a microporous network through the capsule shell. The porosity allows the core material to escape from the crosslinked gelatin microcapsule in proportion to the amount of porosity generated by the removal of the plasticizer. The core material may be allowed to escape quickly or slowly by controlling the amount of plasticizer used in the capsule shell. Generally, plasticizer is added to the gelatin in an amount within the range from about 1% to about 75% by weight of the gelatin component, preferably about 10–65%.

Examples of suitable plasticizer particles for glutaraldehyde-crosslinked gelatins that decrease permeability include sugars, starches, hydrolyzed starches (such as Capsul® made by National Starch and Chemical of Bridgewater, N.J.), cyclodextrins, maltodextrins, corn syrup solids, and sorbitol. Specific starches contemplated for use in the invention include modified corn starches and waxy maize starches. Specific sugars contemplated for use in the invention include sucrose. Specific cyclodextrins contemplated for use in the invention include β-cyclodextrin. For the purposes of the present invention, maltodextrins have a dextrose equivalent of less than 20, and corn syrup solids have a dextrose equivalent of 20 or more. Particularly useful maltodextrins and corn syrup solids that are contemplated for use in the invention are made from waxy maize starch and are commercially available under the trademark STAR-DRI™ as STAR-DRI™ 1, 5, 10, 15, and 20 for the maltodextrins and STAR-DRI™ 24, 35, and 42 for corn syrup solids. The preferred plasticizers are sorbitol and corn syrup solids.

The feeding deterrent component, if used, comprises a cucurbitacin-containing solid particle, powder, or dust. The preferred cucurbitacin-containing solids useful in the present invention are in the form of dried, ground gourd roots as described in Canadian Patent No. 1,195,922, U.S. Pat. No. 4,880,624, and *The Merck Index,* 10th ed., p. 2609 (1983). Briefly summarized, plants in the cucurbitacae order contain small quantities of oxygenated tetracyclic triterpenoid compounds (usually referred to as the cucurbitacins) that are responsible for the bitter taste of the plant tissue. Seventeen of the cucurbitacins have been isolated and identified by letters. If desired, diluted synthetic cucurbitacin may be made and carried on a solid carrier for the present invention. References herein the "cucurbitacin-containing" shall mean plant tissues or carriers containing at least one of the cucurbitacins A, B, C, D, E, F, G, H, I, J, K, L, O, P, Q, R, or glycosides of any of these. Materials containing the E and/or E glycoside cucurbitacins are preferred.

Plant tissues containing the highest levels of cucurbitacins include the roots of the buffalo gourd (*Cucurbita foetidissima*) which, when dried, contain about 0.3 % by weight cucurbitacins. Other cucurbitan-containing materials useful for the invention may come from, inter alia, C. andreana NAUD, C. cylindrata Wats, C. ecuadorensis Cutl. and Whit., C. foetidissima HBK, C. gracilior Bailey, C. lundelliana Bailey, C. martinezii Bailey, C. okeechobensis Bailey, C. palmata Wats., C. palmeri Bailey, C. pedatifolia Bailey, C. sororia Bailey, and C. texana Gray.

Buffalo gourd root powder is the preferred source of cucurbitacin-containing material for use in the invention because the root powder contains a significant quantity of starch. This starch acts as a sticking agent when wetted to assist the applied microcapsules in adhering to the outer surfaces of plants. Such adhesion properties are advantageous when the particles are aerially applied.

The use of cucurbitacin-containing plant tissues has a number of practical benefits. First, the inherent chemical composition of cucurbitacin-containing plant tissue is responsible for the feeding deterrent effects. Cucurbitacin-containing plant tissues can, therefore, be used in a dry form which reduces the special handling and storage concerns with grinding, formulating, and storing moist plant tissues. Moreover, the deterrent effects are exhibited at such low levels that there are no special procedures required for handling the cucurbitacin which is quite toxic in its pure form. Only the core pesticide component might require special handling during manufacture of the microcapsules.

To form the microcapsules of the invention, any method known in the art for encapsulating a core material in a capsule shell may be used to form the microcapsules of the invention. While coacervation may be advantageously used, coextrusion of the core material and the outer layer materials through concentric nozzles is, however, preferred for the control and coating efficiency afforded by extension techniques. A centrifugal extrusion dual concentric nozzle device, a dual concentric dropping nozzle device, a rotating disc device, or a spray nozzle device, each of which are conventional in the microencapsulation art, may be employed.

In a preferred extrusion method, the aqueous encapsulation mixture comprising gelatin and 1% to 75% of the water soluble plasticizer (dry basis) is extruded through the outer nozzle of a concentric nozzle extruder around the core material (with or without a feeding deterrent component) being extruded through the inner nozzle to form a concentric rod of core material surrounded by a sheath of shell solution. Under the effects of surface tension, the concentric rod extrudate breaks into a series of individual droplets having a core droplet surrounded by shell solution. The extruded microcapsules are then either caught in a bath containing a glutaraldehyde solution or the particles are first collected, dried, and subsequently treated with a glutaraldehyde solution to effect crosslinking.

If cucurbitacin-containing solids are used in the capsule shell as a feeding deterrent, the solids are mixed and extruded with the shell solution. The cucurbitacin-containing solids can also be coated on the surface of the microcapsules by collecting the wet microcapsules in a bed of finely divided solids containing the cucurbitacin. The solids would adhere to and become partially imbedded in the surface of the microcapsule. Contain in the capsule shell cement the powder to the surface.

The microcapsules of the invention can be applied using a variety of conventional processes to the soil and plant surfaces in forests, agriculture fields or crops, gardens, and other areas requiring the addition of chemical or biologic agents.

The microcapsules may be applied with any number of conventional methods without significant change in the application method or the formulation preparation procedure. Microcapsules can be dispersed as an aerosol in a nonaqueous carrier. When used as an aerosol, the microcapsules and a spraying agent are sealed in a pressurized container. Spraying agents such as Freon, LP gas, dimethyl ether, carbon dioxide, and vinyl chloride monomer may be used depending on the relevant ecological regulations. Rain water or irrigation of the treated area can be used to release the core material.

The microcapsules can also be sprayed over large areas using conventional aerial spraying techniques. The microcapsules can be sprayed from aqueous or nonaqueous solutions depending on when the core material is to be released. Spraying the microcapsules from an aqueous solution will contact the microcapsule with water in the during the application and start to remove the plasticizer from the shell immediately. Spraying the microcapsules with a nonaqueous solution or broadcasting dry microcapsules will require contact with water from another source after the application is completed, e.g., such as with irrigation, rain, or dew before the plasticizer will be removed from the shell and permit the core material to be released.

Another advantageous use of later release at a desired time is the application of the soil insecticide diazinon to sod farms or golf courses. Diazinon, encapsulated in accordance with the invention, can be dispersed using a non-aqueous carrier. The problem of avian deaths from the inadvertent consumption of diazinon-containing capsules can be avoided by including a feeding deterrent, such as buffalo gourd root powder as part of the core material or, preferably, as an clement of or on the capsule shell. The root powder has a strong bitter taste that will deter consumption of the capsules by birds during the day. Diazinon can be released from the microcapsules by irrigating the fields and dissolving the plasticizer from the shell wall. If the irrigation occurs at night, the diazinon will be released from the granule into the soil while birds are not feeding. The regulatory objections to the use of diazinon on sod farms and golf courses can thereby be overcome.

In addition, the present invention can be prepared with particle sizes much smaller than those of corn cob grit traditionally used as a carrier for diazinon or other soil insecticides. The reduced size will further help to decrease the degree of avian death attributed to mistaken feeding on the applied particles. Moreover, small microcapsules of the present invention will tend to fall deeper into lawn thatch rather than sitting exposed on the surface of a treated lawn thereby reducing the visibility of the applied particles.

Microcapsules of the present invention can also be applied in combination with a granular fertilizer as a coating on the surface of the granule. The combination of products help to reduce the number of applications as well as constituting a granule that is generally not consumed by birds.

The microcapsules can also be applied to animal skin surfaces as a dry powder for release of the core material to the animal skin as the animal sweats and dissolves the plasticizer in the outer shell. In this way, flea powders may be applied with safety and remain efficacious over an extended period of time.

Additional advantages of the microcapsules of the invention include reduced frequency of application, reduced possibility of harm to plants caused by the applied chemical, a high degree of safety in handling the microcapsules, and prevention of environmental pollution.

What is claimed is:

1. A method of controlling the release of a chemical agent comprising:

encapsulating in a microcapsule having a core material surrounded by a shell wall, wherein said core material comprises a chemical agent selected from the group consisting of insecticides, herbicides, plant growth regulators, insect attractants, and insect repellents, and said shell wall comprises a glutaraldehyde cross-linked gelatin which contains a feeding deterrent comprising a cucurbitacin and at least one water soluble plasticizer selected from the group consisting of starches, sugars, cyclodextrins, maltodextrins and sorbitol, wherein the core material is a dry hydrophilic material, a hydrophilic material in a hydrophobic carrier, or a hydrophobic material whereby said plasticizer renders the shell wall impermeable to the core material until said plasticizer is removed by contact with water, and contacting the microcapsule with water at a desired time and location to remove said at least one water soluble plasticizer and form a microcapsule having a porous shell wall whereby the core material from said core permeates through said shell wall.

2. The method of claim 1 wherein contacting the microcapsule with water occurs after applying said microcapsules at a desired location.

3. The method of claim 1 wherein contacting the microcapsules with water occurs while spraying said microcapsule at a desired location.

4. The method of claim 1 wherein the encapsulating step comprises encapsulating said core material in a shell containing enough plasticizer that said core material is released at a sustained rate from said microcapsule following contact with water.

5. The method of claim 1 wherein the encapsulating step comprises encapsulating said chemical agent in a shell wall containing about 1% to about 75% of said at least one water soluble plasticizer.

6. The method of claim 1 wherein the encapsulating step comprises encapsulating a core material comprising either diazinon or paraquat.

7. The method of claim 1 wherein the encapsulating step comprises encapsulating a combination of an insecticide and a polysaccharide gum as said core material.

8. The method of claim 1 wherein the encapsulating step comprises encapsulating said core material in a shell further comprising a cucurbitacin as a feeding deterrent.

9. A method for applying an insecticide by a process comprising:

contacting a microcapsule comprising an outer shell material and an inner core insecticide with water to release the insecticide from within said microcapsule, wherein said insecticide is in the form of a dry hydrophilic material, a hydrophilic material in a hydrophobic carrier, or a hydrophobic material; and wherein said outer shell material is made from a material comprising: (a) a glutaraldehyde cross-linked gelatin which contains at least one water soluble plasticizer selected from the group consisting of starches, sugars, cyclodextrins, maltodextrins and sorbitol whereby said plasticizer renders said shell material impermeable to said insecticide until said plasticizer is removed by contact with water; and (b) a feeding deterrent comprising a cucurbitacin.

10. A method as in claim 9 wherein the contacting step further comprises:

contacting said microcapsule with water wherein said shell material further comprises a cucurbitacin as a feeding deterrent.

11. A method as in claim 9 wherein the contacting step further comprises:

contacting said microcapsule with water wherein the insecticide in said core comprises diazinon.

12. A method for applying an insect repellent by a process comprising:

contacting a microcapsule comprising an outer shell material and an inner core containing an insect repellent with water to release the insecticide from within said microcapsule, wherein said insect repellent is in the form of a dry hydrophilic material, a hydrophilic material in a hydrophobic carrier, or a hydrophobic material; and wherein said outer shell material is made from a material comprising a glutaraldehyde cross-linked gelatin which contains at least one water soluble plasticizer selected from the group consisting of starches, sugars, cyclodextrins, maltodextrins and sorbitol whereby said plasticizer renders said shell material impermeable to said insect repellent until said plasticizer is removed by contact with water.

13. A process for applying diazinon to soil by a process comprising:

applying to soil in a sod farm or golf course microcapsules comprising:

(a) a core material comprising diazinon in (b) a capsule shell wall which completely surrounds said core material, wherein said shell wall material comprises (i) a glutaraldehyde crosslinked gelatin containing 1–75 wt % of at least one water soluble plasticizer selected from the group consisting of water soluble starches, sugars, cyclodextrins, maltodextrins, corn syrup solids, and sorbitol which inhibits transfer of said core material through said crosslinked gelatin; and (ii) a feeding deterrent comprising a cucurbitacin; and contacting said microcapsules with water to remove said plasticizer from said shell wall and permit said diazinon to be released into said soil.

* * * * *